(12) United States Patent
Craig et al.

(10) Patent No.: US 7,293,473 B2
(45) Date of Patent: Nov. 13, 2007

(54) METHOD AND APPARATUS FOR SAMPLING BIOLOGICAL PARTICLES IN AN AIR FLOW

(75) Inventors: William C. Craig, Endicott, NY (US); Stephen J. Gesel, Endicott, NY (US); James P. Neary, Binghamton, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/092,058

(22) Filed: Mar. 29, 2005

(65) Prior Publication Data
US 2006/0225522 A1 Oct. 12, 2006

(51) Int. Cl.
*G01N 1/22* (2006.01)
*G01N 1/40* (2006.01)

(52) U.S. Cl. ............................ 73/863.01; 73/863.21; 73/863.22; 73/863.24; 435/30; 435/45.1; 435/286.1; 435/309.1

(58) Field of Classification Search ............. 73/863.01, 73/863.21–863.25, 31.03, 864.33; 435/286.5, 435/30, 40.51, 286.1, 309.1
See application file for complete search history.

(56) References Cited

U.S. PATENT DOCUMENTS

| | | | | |
|---|---|---|---|---|
| 4,147,500 A | | 4/1979 | Karlsoen | 432/2 |
| 4,230,031 A | | 10/1980 | Pedroso et al. | 98/115 |
| 4,764,758 A | * | 8/1988 | Skala | 73/863.01 X |
| 5,259,854 A | | 11/1993 | Newman | 55/320 |
| 5,412,975 A | | 5/1995 | Raabe et al. | 73/28.04 |
| 5,561,515 A | * | 10/1996 | Hairston et al. | 356/28 |
| 6,087,183 A | | 7/2000 | Zaromb | 436/178 |
| 6,197,093 B1 | | 3/2001 | Wieser-Linhart | 95/196 |
| 6,484,594 B1 | | 11/2002 | Saaski et al. | 73/863.21 |
| 6,520,033 B1 | | 2/2003 | Schroeder et al. | 73/863.12 |
| 6,613,571 B2 | * | 9/2003 | Cordery et al. | 436/48 |
| 6,854,344 B2 | * | 2/2005 | Cornish et al. | 73/863.22 |
| 2002/0062701 A1 | * | 5/2002 | Guldi et al. | 73/863.23 |
| 2002/0124664 A1 | * | 9/2002 | Call et al. | 73/863.22 |
| 2003/0000318 A1 | | 1/2003 | Schroeder et al. | 73/863.23 |
| 2003/0110946 A1 | | 6/2003 | Lehman | 95/273 |
| 2003/0113230 A1 | | 6/2003 | Cordery et al. | 422/68.1 |
| 2003/0114957 A1 | | 6/2003 | Cordery et al. | 700/228 |
| 2003/0118487 A1 | | 6/2003 | Pressman et al. | 422/104 |
| 2003/0131654 A1 | | 7/2003 | Robertson et al. | 73/23.2 |
| 2003/0136179 A1 | | 7/2003 | Felice et al. | 73/31.03 |
| 2003/0145664 A1 | | 8/2003 | Schwarz et al. | 73/863.22 |
| 2003/0152480 A1 | | 8/2003 | Sham | 422/28 |
| 2004/0001783 A1 | | 1/2004 | Bowen | 422/292 |
| 2004/0010379 A1 | | 1/2004 | Craig et al. | 702/22 |
| 2004/0020264 A1 | * | 2/2004 | Megerle | 73/19.01 |
| 2004/0020267 A1 | | 2/2004 | Megerle | 73/31.03 |
| 2004/0022665 A1 | | 2/2004 | Lu | 422/1 |
| 2004/0022673 A1 | | 2/2004 | Protic | 422/28 |
| 2005/0162173 A1 | * | 7/2005 | Mirme | 324/458 |

* cited by examiner

*Primary Examiner*—Thomas P. Noland
(74) *Attorney, Agent, or Firm*—Burns & Levinson LLP; Jacob N. Erlich; David W. Gomes

(57) ABSTRACT

A method and apparatus for sampling potential biohazard particles in an air flow tests for biological particles in the air flow; collects a sample of particulate matter from a specific portion of the air flow in response to an indication in the step of sensing of the presence of biological particles in the specific portion of the air flow, and delays particle movement between the steps of sensing and collecting to coordinate the steps of sensing and collecting to the specific portion of the air flow.

13 Claims, 4 Drawing Sheets

METHOD AND APPARATUS FOR SAMPLING BIOLOGICAL PARTICLES IN AN AIR FLOW

The present invention generally relates to sampling biological particles in an air flow for the purpose of detecting and identifying biohazard particles in the sample, and in particular to performing such sampling in the presence of biological particles.

BACKGROUND OF THE INVENTION

Ever since the anthrax attack in the US Postal Service in 2001, various service organizations which handle deposited envelopes and the like have been keenly interested in developing more effective safeguards against such vulnerability. Among the challenges of such systems are handling a tremendous volume of items, which are processed at high speed and on an almost constant basis, while maintaining sufficient control and order to effectively detect and isolate contaminated items.

SUMMARY OF THE INVENTION

Accordingly, one embodiment of the present invention provides a method for sampling potential biohazard particles in an air flow, comprising the steps of sensing biological particles in the air flow; collecting a sample of particulate matter from a specific portion of the air flow in response to an indication in the step of sensing, of the presence of biological particles in the specific portion of the air flow, and delaying particle movement between the steps of sensing and collecting to coordinate the steps of sensing and collecting to the specific portion of the air flow.

The step of delaying particle movement may include the step of capturing a dry sample of particulate matter from the air flow on a substrate, and the step of collecting may include the step of producing a liquid based sample from the dry sample for analysis of any collected particulate matter in response to an indication of the presence of biological particulate matter in the step of sensing. The step of collecting may include archiving the dry sample of collected particulate matter. The step of sensing may be performed using an archived sample of particulate matter.

The step of collecting may include capturing separate dry samples on separate portions of a moveable substrate. The step of collecting may be performed for a predetermined time period at each separate portion of the substrate. The step of collecting may include moving the substrate to a next sequential separate portion for each sequential predetermined time period. The step of collecting may include halting the capturing and initiating the step of producing in response to the indication in the step of sensing.

The step of delaying particle movement may include passing the air flow through a delay conduit between the steps of sensing and collecting. The method may further comprise the step of diverting the specific portion of the air flow from an exhaust port to the step of collecting in response to the step of sensing. The step of collecting may include the step of capturing a dry sample of particulate matter from the air flow on a substrate.

Another embodiment of the present invention provides a system for sampling potential biohazard particles in an air flow, comprising a sensing device adapted for determining the presence of biological particles in an air flow, a device adapted for collecting a sample of particulate matter from the air flow in response to an indication from the sensing device, of the presence of biological particles, and a delay conduit located to carry the air flow between the sensing device and the device adapted for collecting and adapted to coordinate specific portions of the air flow between the sensing device and the device adapted for collecting, to enable collection of the sample of particulate matter from the specific portions of the air flow in response to an indication from the sensing device, of the presence of biological particles in those specific portions of the air flow.

The system may further comprise a diverter valve affixed to the delay conduit adjacent to the device adapted for collecting and adapted to direct the specific portions of the air flow to the device adapted for collecting in response to the indication from the sensing device. The device adapted for collecting may include a substrate located to be impacted by the air flow. The device adapted for collecting may include a wet sample capture system.

Yet another embodiment of the present invention provides a system for sampling potential biohazard particles in an air flow, comprising a sensing device adapted for determining the presence of biological particulate matter in the air flow, a device adapted for collecting a dry sample of particulate matter from the air flow, and a liquid rinse apparatus adapted for producing a liquid based sample from the dry sample for analysis of any collected particulate matter in response to an indication of the presence of biological particulate matter by the sensing device.

The device adapted for collecting may include a conduit adapted for directing the air flow against a substrate. The device adapted for collecting may be adapted to move the substrate for capturing separate dry samples on separate portions of the substrate. The device adapted for collecting may be adapted to capture dry samples for a predetermined time period at each separate portion of the substrate.

The system may further comprise a valve system adapted to direct the air flow against a specific portion of the substrate for collecting the dry sample and also adapted for alternatively directing a fluid rinse against the specific portion of the substrate for producing the liquid based sample.

BRIEF DESCRIPTION OF THE DRAWINGS

The present invention is illustratively shown and described in reference to the accompanying drawings, in which.

DETAILED DESCRIPTION OF THE DRAWINGS

Figure 1:
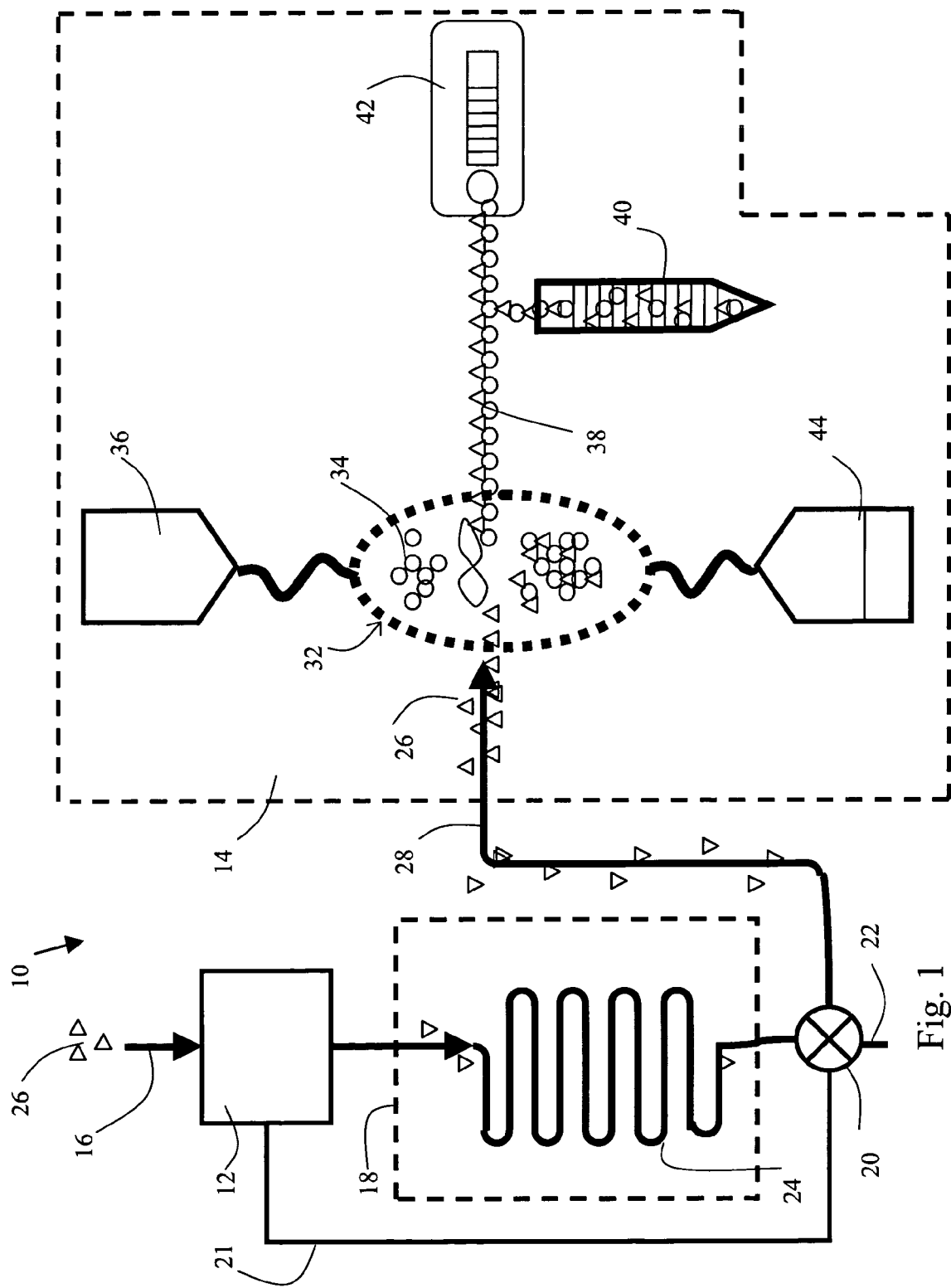
FIG. 1 shows a schematic diagram of a biohazard particle sampling system constructed in accordance with one embodiment of the present invention.

FIG. 1 shows a sampling system 10 generally including a sensing device 12, which is adapted for determining the presence of biological particles, and a sample capture system 14. Sensing device 12 receives an air flow 16 as an input and passes air flow 16 through a conduit 18 to a control valve 20 and exhaust 22. Sensing device 12 is coupled to control valve 20 by control line 21 to divert air flow 16 within conduit 18 to sample capture system 14. Conduit 18 further includes a delay conduit 24 located before control valve 20, which delay conduit 24 delays the passage of air flow 16 to allow time for the sensing for biological particles by sensing device 12. Thus, sensing device 12 is provided with a time delay of several seconds or more to detect biological particles in specific portions of air flow 16 and still allow the diversion of those specific portions of air flow 16 to sample capture system 14.

Sensing device 12 is intended to determine the presence of potentially hazardous biological particles. Sensing device 12 may take any suitable form and may distinguish potentially hazardous biological particles by any suitable methods. For example, particles may first be filtered to collect a particular size range corresponding to particles known to be hazardous, and those collected particles may then be tested for biological content. Any suitable method can be used to distinguish between biological and non-biological particles, such as use of the ultraviolet (UV) light spectrum, which causes natural fluorophores that exist in tissue and cells to fluoresce over well-defined spectral regions. A suitable instrument may use a conventional Laser or LED-based UV Fluorescence Particle Counter.

In response to a positive detection of biological particles by sensing device 12, air flow 16, including biological particles 26, is diverted by a control valve 20, along a collection conduit 28 into sample capture system 14. Air flow 16 and biological particles 26 are directed into a wetted sampler 32, into which is also fed a collection fluid 34 from a reservoir 36. Particles 26 are mixed with and entrained in collection fluid 34 within wetted sampler 32, and the combination is drawn from wetted sampler 32 along a fluid conduit 38, while excess fluid and biological particles within wetted sampler 32 are drained into a waste reservoir 44. Conduit 38 delivers the combined collection fluid and biological particles 26 to both a sample vial 40 for remote sensing and also to a local sensing device 42. Local sensing device 42 provides an immediate indication of the presence of biohazard particles, while sample vial 40 enables a more detailed analysis.

Figure 2:
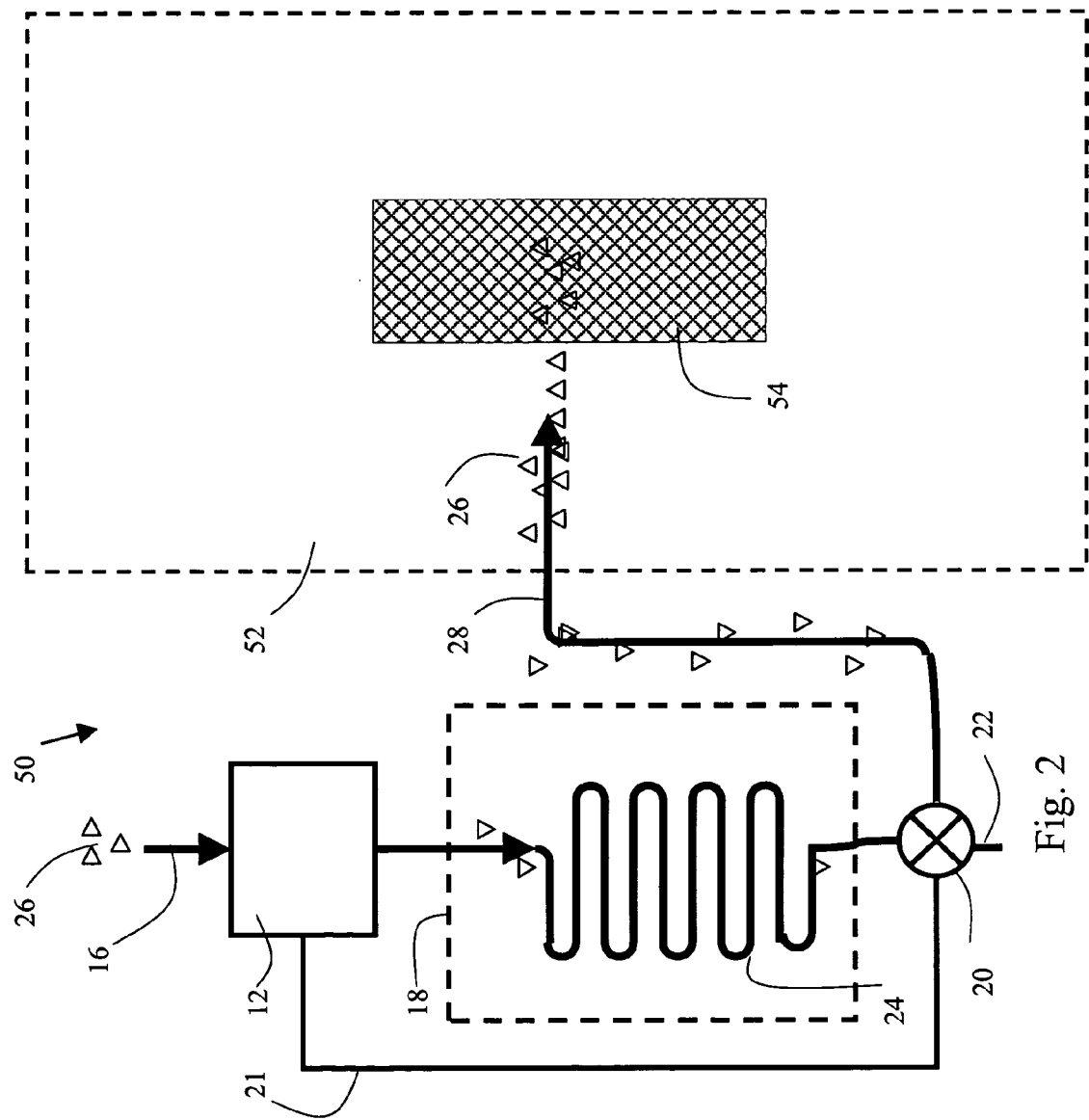
FIG. 2 shows an alternate embodiment of a biological particle sampling system of FIG. 1 constructed with a dry sample capture system.

FIG. 2 shows a biological particle sampling system 50, which is very similar to system 10 (FIG. 1), except for the use of a dry capture system 52. Biological particles 26 in the air flow enter the dry sample capture system 52 through conduit 28 and are directed at a substrate 54. Substrate 54 may be provided in any suitable form adapted to capture particles within the air flow, and thus, might typically be either a filter or a sticky surface, both of which methods are currently known.

Figure 3:
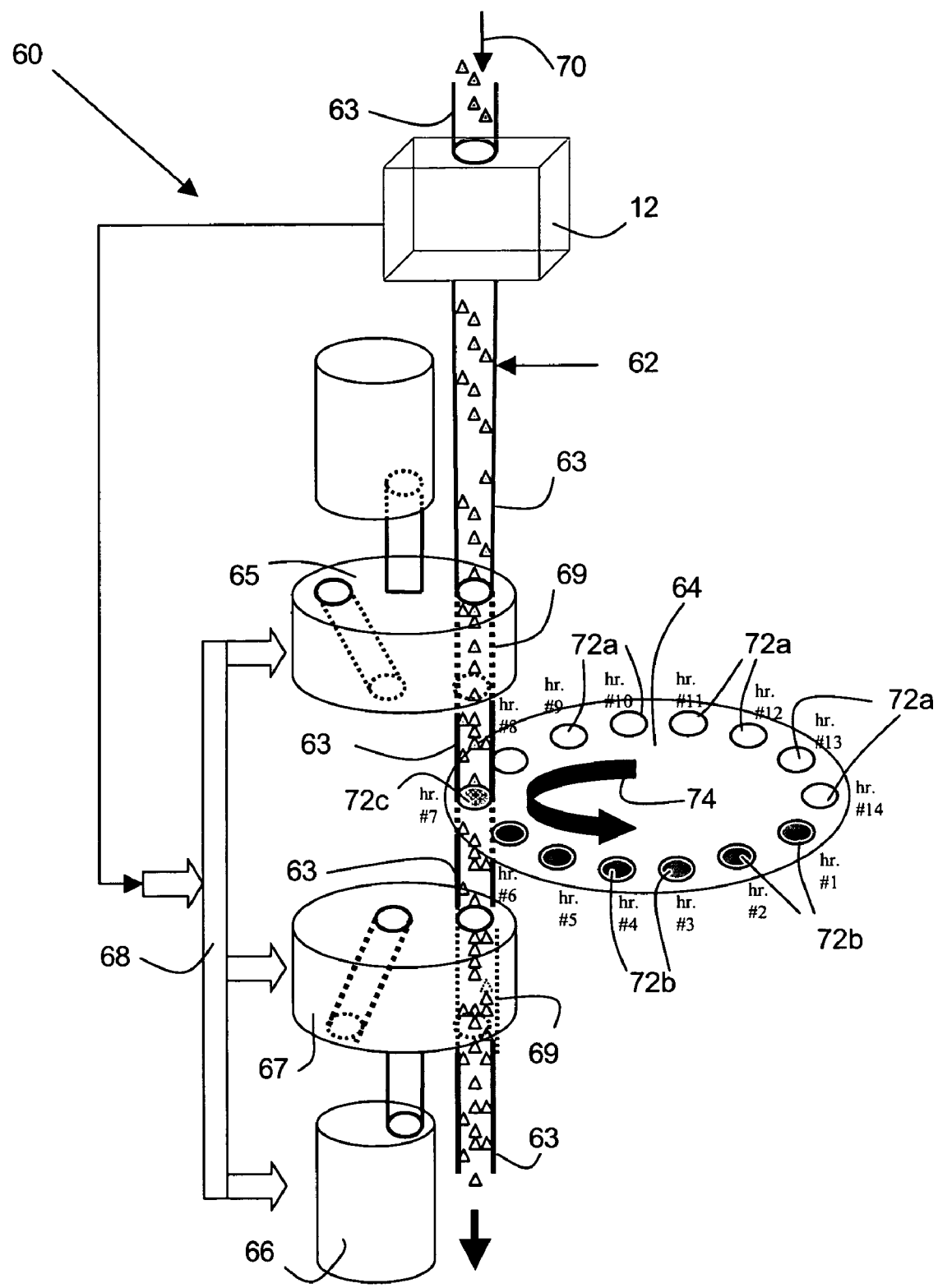
FIG. 3 is a representational diagram of a biohazard particle sampling system constructed in accordance with another embodiment of the present invention.

FIG. 3 shows a biological particle sampling system 60, which generally includes an air flow conduit 62, a biological particle sensing device 12, a particle capture substrate 64, a collection fluid reservoir 66 and a valve system 68 for directing collection fluid to substrate 64. The form and function of sensing device 12 is identical to that described in reference to FIG. 1.

Air flow conduit 62 generally includes a multiplicity of fixed sections 63 interconnected by a pair of valves 65, 67. Valves 65, 67 are a part of valve system 68 and are shown in the air flow position in FIG. 3. In this air flow position of FIG. 3, each valve 65, 67 includes a conduit 69, which forms a continuous air flow conduit 62 with respective adjacent fixed sections 63.

Substrate 64 may take any suitable form and is shown as a circular filter having multiple filter zones 72a, 72b, 72c, with a current filter zone 72c positioned within air flow conduit 62 between adjacent fixed conduit sections 63. Filter zones 72a, 72b, 72c are distinguished from one another by the angular rotation of substrate 64 with respect to air flow conduit 62. Each filter zone 72a, 72b, 72c is used in turn to collect particle samples from air flow 70 for a predetermined time period while the current zone 72c is aligned with air flow conduit 62. At the end of this time period, the current filter zone 72c retains a collection of particles from air flow 70 for its respective time period, and substrate 64 is rotated in the direction of arrow 74 to the next sequential unused filter zone 72a. In this manner, particle samples from each respective time period may be archived for future reference.

Figure 4:
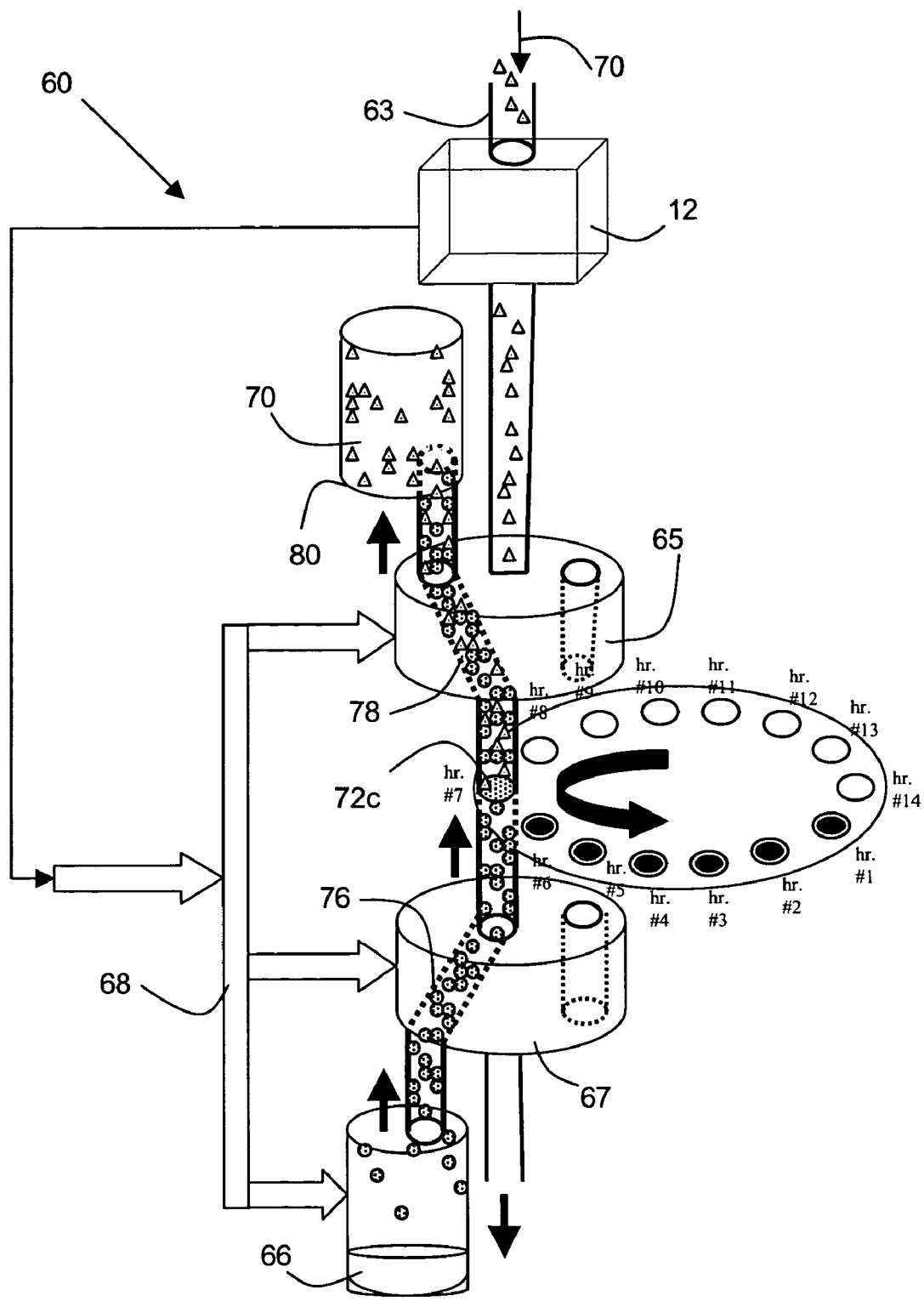
FIG. 4 is a representational diagram of the sampling system of FIG. 3, showing valve system 68 located in a different functional position.

FIG. 4 is another view of system 60 with valve system 68 and valves 65, 67 located in a fluid rinse position to connect fluid collection reservoir 66 with the current filter zone 72c. In this fluid rinse position, valves 65, 67 include respective fluid conduits 76, 78 which direct sample collection fluid from reservoir 66 through current collection zone 72c and in to a sample collection vial 80.

In operation, air flow 70 is directed through current filter zones 72c. In the event that biological particles are detected in air flow 70 by sensing device 12, valve system 68 is activated to move valves 65, 67 to the fluid rinse position of FIG. 4 to collect retained particles in a fluid medium from the current filter zone 72c for purposes of analysis for biohazard particles. In the fluid rinse position of FIG. 4, fluid is pumped from reservoir 66, through respective filter zone 72c and into a sample collection vial 80. An assay strip may also be made available in the same manner described in reference to system 10 (FIG. 1).

The use of a circular filter 64, as represented in FIGS. 3 and 4, enables construction of a system 60 having a simplified operating procedure for handling such filters. A suitable control system would also be provided for all of the embodiments disclosed herein in accordance with known control technology. Any desired level of control may be provided, thus allowing adaptation of the present invention to any application from a simplified, man-portable, field unit to a highly flexible, laboratory instrument.

The present invention is illustratively described above in reference to the disclosed embodiments. Various modifications and changes may be made to the disclosed embodiments by persons skilled in the art without departing from the scope of the present invention as defined in the appended claims. For example, filter 64 may be linear instead of circular and it may move continuously rather than in discrete steps. Further, valve system 68 may not be used if air flow samples are collected at one position on filter 64 while liquid samples are retrieved at an adjacent portion of filter 64 which has most recently been used for collecting samples from the air flow. Variants may include, but are not limited to, pre-packaged, automated, or disposable components depending on application.

What is claimed is:

1. A method for sampling potential biohazard particles in an air flow, comprising the steps of:
   sensing for biological particles in the air flow;
   collecting a sample of particulate matter from a specific portion of the air flow in response to an indication, in said step of sensing, of the presence of biological particles in said specific portion of the air flow; and
   delaying particle movement between said steps of sensing and collecting to coordinate said steps of sensing and collecting to said specific portion of the air flow,
   wherein said step of delaying particle movement includes passing the air flow through a delay conduit between said steps of sensing and collecting.

2. The method of claim 1, further comprising the step of diverting said specific portion of the air flow from an exhaust port to said step of collecting in response to said step of sensing.

3. The method of claim 1, wherein said step of collecting includes the step of capturing a dry sample of particulate matter from said air flow onto a substrate.

4. The method of claim 3, wherein said step of collecting includes the step of producing a liquid based sample from the dry sample for analysis of any collected particulate matter in response to an indication of the presence of biological particulate matter in said step of sensing.

5. The method of claim 4, wherein said step of collecting further includes archiving the dry sample of collected particulate matter.

6. The method of claim 5, wherein said step of producing is performed using an archived sample of particulate matter.

7. The method of claim 4, wherein said step of collecting further includes capturing separate dry samples on separate portions of a moveable substrate.

8. The method of claim 7, wherein said step of collecting is performed for a predetermined time period at each separate portion of the substrate.

9. The method of claim 8, wherein said step of collecting further includes moving the substrate to a next sequential separate portion for each sequential predetermined time period.

10. A system for sampling potential biohazard particles in an air flow, comprising:

a sensing device adapted for determining the presence of biological particles in an air flow;

a device adapted for collecting a sample of particulate matter from the air flow in response to an indication from said sensing device of the presence of biological particles; and a delay conduit located to carry said air flow between said sensing device and said device adapted for collecting and adapted to coordinate specific portions of said air flow between said sensing device and said device adapted for collecting to enable collection of said sample of particulate matter from said specific portions of said air flow in response to an indication from said sensing device of the presence of biological particles in those specific portions of the air flow.

11. The system of claim 10, further comprising a diverter valve affixed to said delay conduit adjacent to said device adapted for collecting and adapted to direct said specific portions of said air flow to said device adapted for collecting in response to said indication from said sensing device.

12. The system of claim 10, wherein said device adapted for collecting includes a substrate located to be impacted by the air flow.

13. The system of claim 10, wherein said device adapted for collecting includes a wet sample capture system.

* * * * *